(12) United States Patent
Achtzehn et al.

(10) Patent No.: US 7,131,345 B2
(45) Date of Patent: Nov. 7, 2006

(54) DEVICE FOR INSPECTING PLANT PARTS LOCATED UNDER WATER

(75) Inventors: Hans-Jürgen Achtzehn, Adelsdorf (DE); Robert Staudigel, Höchstädt (DE)

(73) Assignee: IntelligeNDT Systems & Services GmbH & Co. KG, Erlangen (DE)

( * ) Notice: Subject to any disclaimer, the term of this patent is extended or adjusted under 35 U.S.C. 154(b) by 86 days.

(21) Appl. No.: 10/825,749

(22) Filed: Apr. 15, 2004

(65) Prior Publication Data

US 2004/0221666 A1   Nov. 11, 2004

(30) Foreign Application Priority Data

Apr. 15, 2003   (DE) ................. 103 17 191

(51) Int. Cl.
*G21C 17/013* (2006.01)
*G01M 19/00* (2006.01)
*G01B 17/08* (2006.01)

(52) U.S. Cl. ................. 73/865.8; 73/598; 73/618; 73/866.5; 405/190; 405/191; 702/39; 976/DIG. 213

(58) Field of Classification Search ............. 73/865.8, 73/866.1, 866.3, 866.5, 86, 618, 633, 151, 73/598; 74/457, 458, 459.5, 460; 356/3.03; 405/190, 191; 702/39; 976/DIG. 213
See application file for complete search history.

(56) References Cited

U.S. PATENT DOCUMENTS 3,550,386 A * 12/1970 Ballinger .............. 405/191
4,196,049 A * 4/1980 Burns et al. ............ 376/249
4,502,407 A * 3/1985 Stevens .................. 114/222
5,156,050 A   10/1992 Schmid et al.
5,193,405 A   3/1993 Oomichi et al.
5,959,211 A * 9/1999 Wagner et al. ............ 73/634

FOREIGN PATENT DOCUMENTS

| EP | 0 452 516 A1 | 10/1991 |
| EP | 0 461 506 B1 | 12/1991 |
| EP | 0 528 622 A1 | 2/1993 |
| JP | 55 018 903 | 2/1980 |
| JP | 60 201 250 | 10/1985 |
| JP | 04240597 A | 8/1992 |
| JP | 2000 338 291 | 12/2000 |

OTHER PUBLICATIONS

Framatome ANP GMBH: "Visual Inspection, Siemens-Underwater-System for Inspections, SUSI 420", outage services.

* cited by examiner

*Primary Examiner*—Hezron Williams
*Assistant Examiner*—David A. Rogers
(74) *Attorney, Agent, or Firm*—Laurence A. Greenberg; Werner H. Stemer; Ralph E. Locher

(57) ABSTRACT

A device for inspecting submersed plant parts is particularly suited for ultrasonic inspection of screws in the core baffle of a nuclear reactor pressure vessel. The device includes a remote-controlled underwater vehicle that is provided at its end face with a carrier that can be pivoted about a pivot axis oriented parallel to the longitudinal central axis of the underwater vehicle, and is provided with a holding device for an inspection head that is arranged on the carrier spaced apart from the pivot axis.

12 Claims, 2 Drawing Sheets

DEVICE FOR INSPECTING PLANT PARTS LOCATED UNDER WATER

BACKGROUND OF THE INVENTION

Field of the Invention

The invention relates to a device for inspecting plant parts that are submersed under water, in particular for ultrasonic inspection of screws in the core baffle of a nuclear reactor pressure vessel.

It is necessary in a range of applications to undertake inspection of safety-related plant parts located at points under water that are difficult to access. Such a safety-related plant part is, for example, the screws with which the core baffle is fastened on the core barrel in the reactor pressure vessel of a nuclear reactor. In order to permit ultrasonic inspection of these screws, it is necessary to position an ultrasonic inspection head on the head of the screw by remote control with the aid of a manipulator, arranged outside the refueling cavity, in a water depth of up to 10 m.

Instead of the use of a manipulator arranged outside the refueling cavity, for the purpose of inspecting a cladding of a fuel pit, Japanese patent application JP 042 40 597 A, for example, discloses using a remote-controlled underwater vehicle fitted with an ultrasonic inspection head. However, because of the drives, illuminating devices and cameras required for it to be freely maneuverable, such an underwater vehicle has a relatively high intrinsic weight and, not least, because of a relatively voluminous float required thereby also has correspondingly large dimensions. It is therefore not not readily possible to approach points in the region of interior edges, for example the screws in the corner regions of the core baffle of a nuclear reactor pressure vessel.

In order to be able to use such an underwater vehicle also to position the inspection head at points that are difficult of access, it has become known in principle from U.S. Pat. No. 5,193,405 and European patent EP 0 461 506 B1 to arrange the inspection head at the free end of a manipulator arm having six axes. However, controlling such a freely movable manipulator arm is complicated, and because of the torques exerted by the force of gravity on the freely floating underwater vehicle as a function of the position of the manipulator arm, it is difficult to keep the vehicle in a stationary floating state. For these reasons, the prior art underwater vehicle is provided with a plurality of suction cups with the aid of which it must be fixed on a smooth surface. The field of use is thus limited to plant parts with smooth walls.

SUMMARY OF THE INVENTION

It is accordingly an object of the invention to provide an inspection device for submersed plant parts which overcomes the above-mentioned disadvantages of the heretofore-known devices and methods of this general type and which provides for an underwater vehicle that is not technically complicated and can also be used in the corner regions of a core baffle.

With the foregoing and other objects in view there is provided, in accordance with the invention, a device for inspecting submersed plant parts, comprising:

a remote-controlled underwater vehicle having an end face and a longitudinal central axis perpendicular to the end face;

a carrier pivotally mounted at the end face exclusively about a pivot axis oriented parallel to the longitudinal central axis of the underwater vehicle; and a holding device for an inspection head mounted to the carrier at a spacing distance from the pivot axis.

The device is, in particular, configured for ultrasonic inspection of plant parts such as screws in a core baffle of a nuclear reactor pressure vessel.

In other words, the device includes a remote-controlled underwater vehicle that is provided at an end face with a carrier that can be pivoted or rotated exclusively about a pivot axis that is oriented parallel to a longitudinal central axis, running perpendicular to the end face, of the underwater vehicle. There is also provided a holding device for an inspection head that is arranged on the carrier at a spacing from the pivot axis. It is possible by this measure to move the inspection head into different positions relative to the underwater vehicle with the underwater vehicle stationary, and so it is also possible to inspect plant parts that are located offset from the longitudinal central axis of the underwater vehicle.

In a particularly advantageous refinement of the invention, the carrier provided with the test head is balanced out in such a way that virtually no torque acting on the carrier about the pivot axis is exerted by the force of gravity irrespective of the pivoting position of the inspection head. Owing to this measure, different inspection positions can be approached with a freely floating underwater vehicle without the need of further complicated control measures for balancing and maintaining the floating state.

In accordance with an added feature of the invention, the pivot axis is disposed at a spacing from the longitudinal central axis. Preferably, the pivot axis is disposed at an edge of the underwater vehicle. It is advantageous when the location and orientation of the pivot axis on the underwater vehicle and a spacing of the holding device from the pivot axis are coordinated with one another such that the inspection head can be brought into mutually opposite positions that project over a lateral edge of the underwater vehicle, or extend at least into a vicinity of it.

In accordance with an additional feature of the invention, there are provided a multiplicity of support elements on the carrier. They are disposed in a circumferential direction about the pivot axis and spaced apart from one another in the circumferential direction.

In accordance with another feature of the invention, a universal joint is provided for mounting the inspection head in the holding device.

In accordance with a further feature of the invention, the carrier comprises a ring having a center on the pivot axis, the ring is fixed on a shaft of a first rotary drive with at least one radial spoke.

In a preferred embodiment, the carrier is an optically transparent disc.

In accordance with a concomitant feature of the invention, the inspection head is rotatably mounted in the holding device about a central axis extending parallel to the pivot axis.

Other features which are considered as characteristic for the invention are set forth in the appended claims.

Although the invention is illustrated and described herein as embodied in a device for inspecting plant parts located under water, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
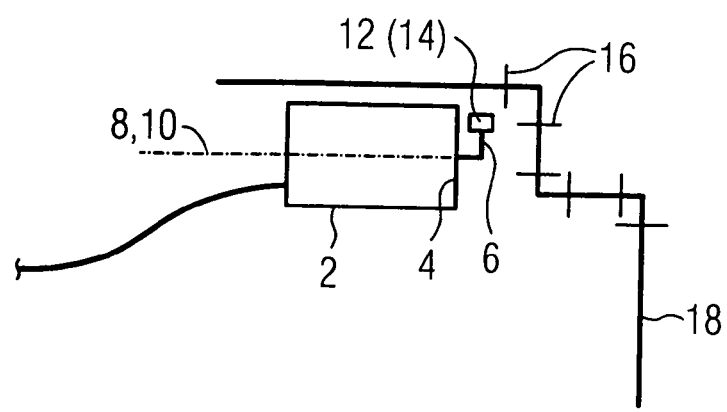
FIG. 1 is a schematic outline view of a device in accordance with the invention during use for ultrasonic inspection of screws in the core baffle of a nuclear reactor pressure vessel.

Referring now to the figures of the drawing in detail and first, particularly, to FIG. 1 thereof, the device comprises a basic vehicle in the form of a remote-controlled underwater vehicle 2. Such a vehicle is known, for example, under the trade name SUSI from Framatome ANP GmbH, of Germany. In accordance with the invention, the underwater vehicle 2 is provided at its end face 4 with a carrier 6 that is pivotally mounted on the underwater vehicle 2 about a pivot axis 10 oriented parallel to the longitudinal central axis 8, running perpendicular to the end face 4, of the underwater vehicle 2. A holding device 12 is disposed on the carrier 6 at a spacing from the pivot axis 10. The holding device 12 is fitted with an inspection head 14, an ultrasonic inspection head in the exemplary embodiment, such as is known, for example, from European patent application EP 0 452 516 A1.

FIG. 1 illustrates a situation such as arises from an ultrasonic inspection of screws 16 in the core baffle 18 of a reactor pressure vessel. As illustrated in FIG. 1, a multiplicity of these screws 16 are located in corner positions of the core baffle 18 that cannot be directly (centrally) approached because of the relatively large dimensions of the underwater vehicle 2. It is now possible to use the rotary or pivotable carrier 6 to inspect screws 16 in corner positions even when the underwater vehicle 2 is located laterally offset from these corner positions.

Figure 2:
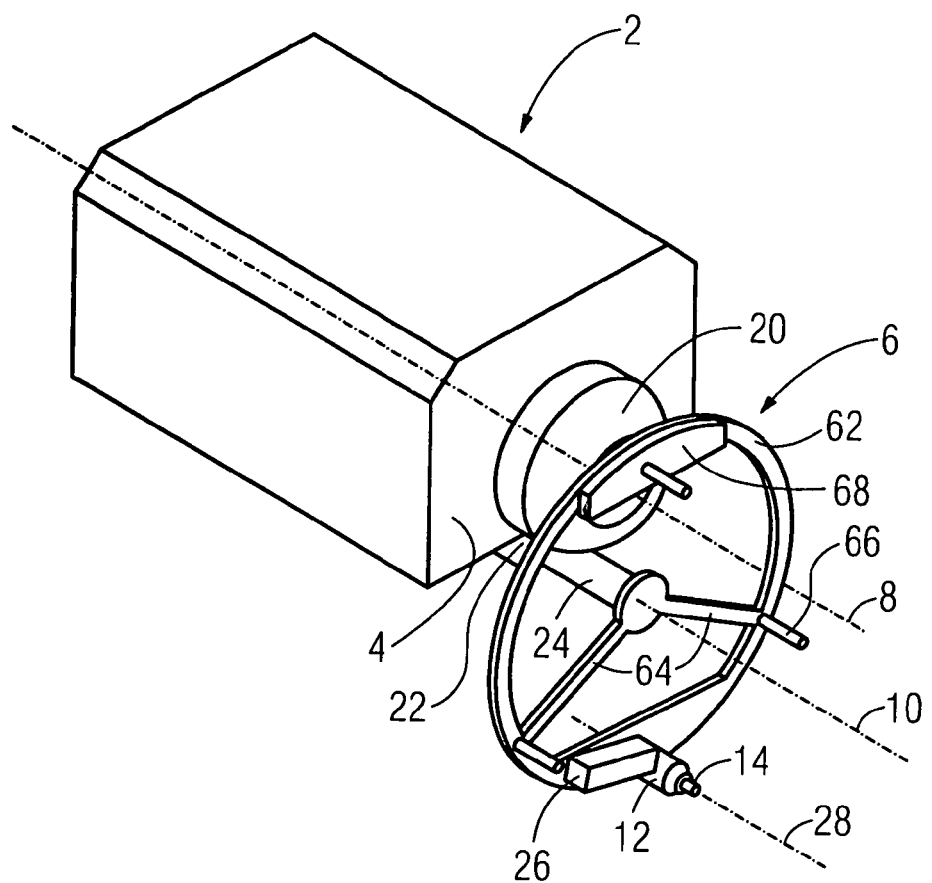
FIG. 2 is a perspective view of the device according to the invention.

In accordance with FIG. 2, the underwater vehicle 2 (drawn only schematically) is provided on its end face 4 with a camera 20 with integrated illumination, which can be used for visual monitoring of the traveling motion of the underwater vehicle 2. Arranged on the underside of the underwater vehicle 2 is a first rotary drive 22 with a shaft 24 on which the carrier 6 is fastened at the end face. The carrier 6 is constructed in the exemplary embodiment from a ring 62 that is fixed via spokes 64 at the end face on the shaft 24 and can be pivoted—in the exemplary embodiment it can be endlessly rotated—about the pivot axis 10. The holding device 12 is disposed on the ring 62. The inspection head 14 is mounted in the holding device by universal joint. A second rotary drive 26 permits the inspection head 14 to be rotated about its central axis 28 in order to enable correct placement on the screw head, for example an internal polygon. Electric sliprings (not illustrated in the figures) serve to supply power to the two rotary drives, and to supply the ultrasonic inspection head 14. This renders endless rotation of the carrier 6 possible.

A plurality of support elements 66, axially parallel pins in the example, are disposed on the end face of the ring 62; in the event of faulty positioning they prevent damage to the inspection head 14 and serve for aligning the underwater vehicle 2 (longitudinal axis perpendicular to the wall).

Moreover, a balancing weight 68 is located opposite the inspection head 14 for the purpose of balancing out a weight load. In other words: the carrier 6 provided with the inspection head 14 is balanced out in such a way that the force of gravity exerts virtually no torque acting on the carrier 6 about the pivot axis 10 irrespective of the rotational position of the inspection head 6. This measure facilitates the maintenance of a stationary floating state even when there is a rotary movement of the carrier 6, and thereby facilitates the approach to the inspection position.

Figure 3:
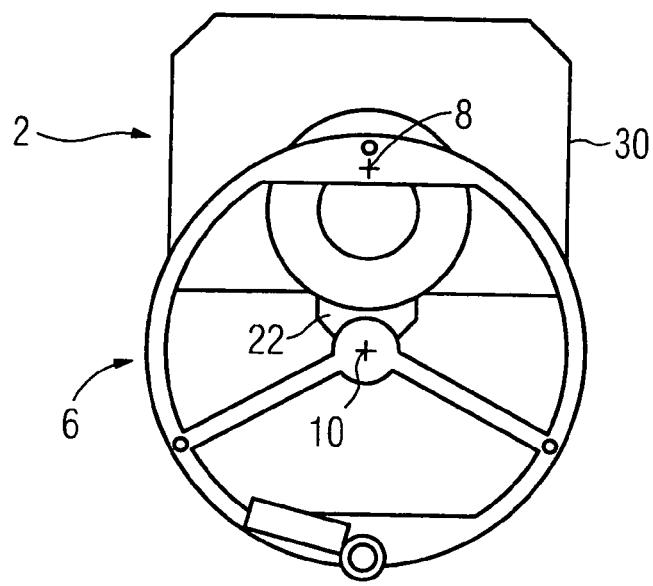
FIG. 3 is an elevational view of the end face of the device.

It may be seen in the plan view of the end face in accordance with FIG. 3 that the inspection head 14 can be brought into lateral positions by rotating the carrier 6 about the pivot axis 10. The latter is located at a spacing distance from the longitudinal central axis 8 at the edge, below the underwater vehicle in the example. These positions are approximately aligned with the lateral edge 30, that is to say the lateral rim of the underwater vehicle 2.

Instead of a ring 62 illustrated in the figures, it is also possible to provide a transparent disk made from plastic as carrier 12 for the inspection head 14.

Figure 4:
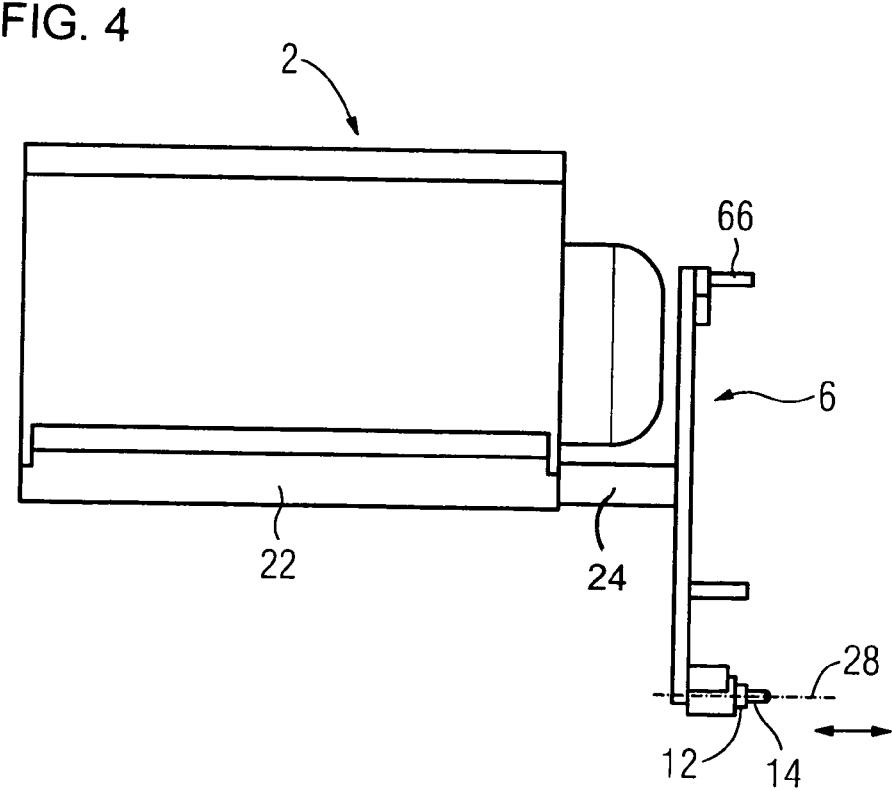
FIG. 4 is a side elevational view of the device according to the invention.

In accordance with FIG. 4, the inspection head 14 is mounted in the holding device 12 in a resilient fashion in the direction of its transmitting or central axis 28. This is illustrated by the double arrow. The support elements 66 compel an axially parallel position of the inspection head 14 relative to the screw to be inspected, and prevent the inspection head 14 from being overloaded or damaged by the underwater vehicle 2 drifting away to the side.

The inspection head 14 is now positioned over the screw head with the aid of the underwater vehicle 2, and applied flush to the screw head by appropriately controlling the drive units of the underwater vehicle 2. The correct positioning and coupling can be monitored with the aid of the echo signals picked up by the inspection head 14. The drive units arranged in the underwater vehicle 2 hold the inspection head 14, by exerting a slight contact pressure on the screw head, until the inspection is terminated. Further docking measures for holding the inspection position are not required because of the precision of the control of the underwater vehicle 2.

This application claims the priority, under 35 U.S.C. § 119, of German patent application No. 103 17 191.6, filed Apr. 15, 2003; the disclosure of the prior application is herewith incorporated by reference in its entirety.

We claim:

1. A device for inspecting submersed plant parts, comprising:
   a free floating remote-controlled underwater diving vehicle having drives disposed thereon for approaching different inspection positions, an end face and a longitudinal central axis perpendicular to said end face;
   a carrier pivotally mounted at said end face exclusively about a pivot axis oriented parallel to said longitudinal central axis of said underwater vehicle, said carrier including a ring having a center on said pivot axis;
   at least one radial spoke fixing said ring on a shaft of a first rotary drive; and
   a holding device for an inspection head mounted to said carrier at a spacing distance from said pivot axis.

2. The device according to claim 1, wherein said pivot axis is disposed at a spacing from said longitudinal central axis.

3. The device according to claim 2, wherein said pivot axis is disposed at an edge of said underwater vehicle.

4. The device according to claim 3, wherein a location of said pivot axis on said underwater vehicle and a spacing of said holding device from said pivot axis are coordinated with one another such that the inspection head can be brought into mutually opposite positions that project over a lateral edge of said underwater vehicle.

5. The device according to claim 3, wherein a location of said pivot axis on said underwater vehicle and a spacing of said holding device from said pivot axis are coordinated with one another such that the inspection head can be brought into mutually opposite positions in a vicinity of or projecting beyond a lateral edge of said underwater vehicle.

6. The device according to claim 1, wherein said underwater vehicle is configured for inspection of plant parts in a core baffle of a nuclear reactor pressure vessel.

7. The device according to claim 1, wherein said holding device is configured for holding an inspection head for ultrasonic inspection of screws in a core baffle of a nuclear reactor pressure vessel.

8. The device according to claim 1, wherein said carrier is balanced such that, when the test head is mounted to said carrier, substantially no torque acting on said carrier about said pivot axis is exerted by a force of gravity irrespective of a pivoting position of the inspection head.

9. The device according to claim 1, which comprises a multiplicity of support elements on said carrier and disposed in a circumferential direction about said pivot axis and spaced apart from one another in the circumferential direction.

10. The device according to claim 1, which comprises a universal joint mounting the inspection head in said holding device.

11. The device according to claim 1, wherein said carrier is an optically transparent disc.

12. The device according to claim 1, wherein the inspection head is rotatably mounted in said holding device about a central axis extending parallel to said pivot axis.

* * * * *